(12) United States Patent
Ongaro et al.

(10) Patent No.: US 9,511,157 B2
(45) Date of Patent: Dec. 6, 2016

(54) STEAM STERILISER

(71) Applicant: ABSOLUTE UP S.R.L., Villa di Serio (BG) (IT)

(72) Inventors: Daniele Ongaro, Villa di Serio (IT); Mariapia Ghilardi, Villa di Serio (IT)

(73) Assignee: ABSOLUTE UP S.R.L., Villa di Serio (BG) (IT)

( * ) Notice: Subject to any disclaimer, the term of this patent is extended or adjusted under 35 U.S.C. 154(b) by 0 days.

(21) Appl. No.: 14/367,548

(22) PCT Filed: Dec. 10, 2012

(86) PCT No.: PCT/IB2012/057123
§ 371 (c)(1),
(2) Date: Jun. 20, 2014

(87) PCT Pub. No.: WO2013/093700
PCT Pub. Date: Jun. 27, 2013

(65) Prior Publication Data
US 2014/0334977 A1    Nov. 13, 2014

(30) Foreign Application Priority Data
Dec. 21, 2011    (IT) ................ MI2011A2334

(51) Int. Cl.
*A61L 2/07*   (2006.01)
*C02F 1/00*   (2006.01)

(52) U.S. Cl.
CPC ............ *A61L 2/07* (2013.01); *C02F 1/001* (2013.01); *A61L 2202/24* (2013.01); *C02F 2303/04* (2013.01)

(58) Field of Classification Search
CPC .................. A61L 2/07; C02F 1/001
See application file for complete search history.

(56) References Cited

U.S. PATENT DOCUMENTS 3,436,173 A * 4/1969 Power .............. A61L 2/206
                                                    312/31
5,122,344 A * 6/1992 Schmoegner ....... A61L 2/18
                                                    422/111

(Continued)

FOREIGN PATENT DOCUMENTS

DE    38 41 930 A1    6/1990
DE    198 60 290 A1   6/2000

(Continued)

OTHER PUBLICATIONS

The PCT Publication WO 2013/093700 A3 containing the International Search Report for International Application No. PCT/IB2012/057123, six pages, mailed Aug. 28, 2013.

*Primary Examiner* — Regina M Yoo
(74) *Attorney, Agent, or Firm* — Vorys, Sater, Seymour & Pease LLP

(57) ABSTRACT

Provided is a steam sterilizer for medical instruments including a feeding system configured to feed a sterilization chamber and including at least one main tank for containing a sterilization fluid; an evacuation system configured to evacuate a discharge fluid from the sterilization chamber; and a purification system configured to draw one of the fluids out of one of the systems and to introduce it into the main tank, and including cleaning means configured to filter the fluid.

3 Claims, 1 Drawing Sheet

(56) References Cited

U.S. PATENT DOCUMENTS

| | | | | |
|---|---|---|---|---|
| 5,348,711 | A * | 9/1994 | Johnson | A61L 2/20 134/166 R |
| 5,556,607 | A * | 9/1996 | Childers | A61L 2/20 134/166 R |
| 5,880,438 | A | 3/1999 | Parrini et al. | |
| 6,656,423 | B1 * | 12/2003 | Joslyn | A61L 2/04 210/175 |
| 8,721,983 | B2 * | 5/2014 | Yokoi | A61L 2/208 422/211 |
| 2005/0112026 | A1 * | 5/2005 | Hill | C12Q 1/22 422/68.1 |
| 2005/0148819 | A1 * | 7/2005 | Noguchi | A61B 1/00059 600/133 |
| 2005/0224493 | A1 * | 10/2005 | Varma | A61C 19/002 219/679 |
| 2006/0057021 | A1 * | 3/2006 | Sawyer | A61L 2/24 422/26 |
| 2008/0014113 | A1 * | 1/2008 | Centanni | A61L 2/202 422/27 |
| 2008/0063574 | A1 * | 3/2008 | Centanni | A61L 2/202 422/108 |
| 2008/0217316 | A1 * | 9/2008 | Ongaro | A61L 2/07 219/407 |
| 2009/0047173 | A1 * | 2/2009 | Mielnik | A61L 2/206 422/28 |
| 2010/0189607 | A1 * | 7/2010 | Yokoi | A61L 2/208 422/116 |
| 2011/0027146 | A1 * | 2/2011 | Yokoi | A61L 2/208 422/211 |
| 2013/0236373 | A1 * | 9/2013 | Tremblay | A61L 2/202 422/292 |
| 2013/0302207 | A1 * | 11/2013 | Ahiska | A61L 2/208 422/3 |

FOREIGN PATENT DOCUMENTS

| | | |
|---|---|---|
| EP | 1 852 131 A1 | 11/2007 |
| GB | 2 428 196 A | 1/2007 |

* cited by examiner

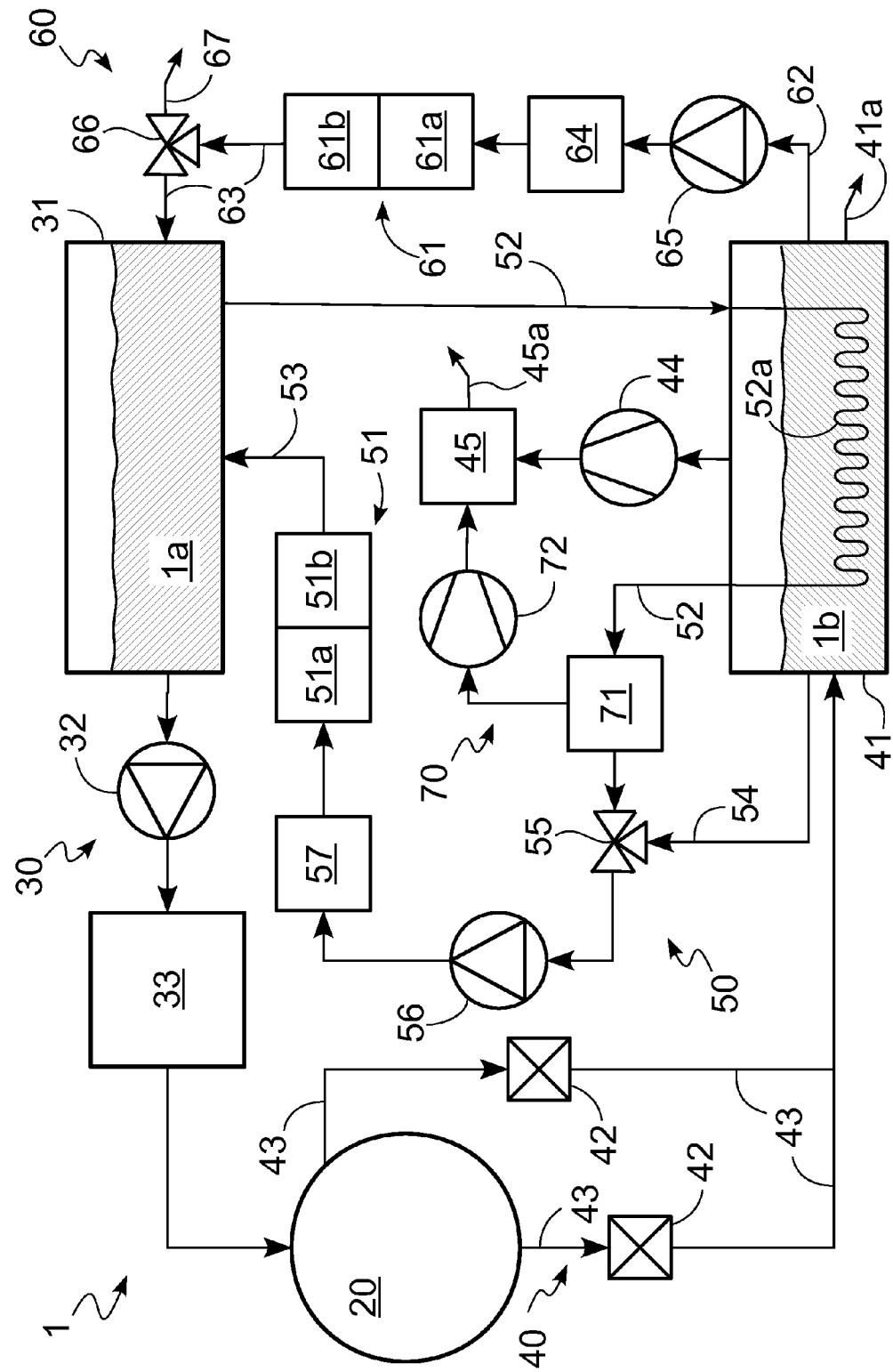

STEAM STERILISER

The present invention relates to a steam sterilizer of the type as recited in the preamble of Claim 1.

In detail, the invention concerns a steam sterilizer for sterilizing/disinfecting surgical or dental instruments, hereinafter simply referred to as medical instruments, using saturated steam at very high temperatures and pressures.

As is known, during any operation, the use of medical instruments that have been sterilized to a high standard is of fundamental importance in order to prevent infection or other similar problems.

For that purpose, various kinds of sterilizers have been conceived, which use different methods in order to permit said instruments to be sterilized/disinfected to a high standard.

One example of such sterilizers are chemical sterilizers which disinfect equipment using chemical substances such as, for example, ethylene oxide or ethoxide.

Another type of sterilizers are plasma sterilizers which sterilize medical equipment using a gas, for example hydrogen peroxide in the plasma state.

These two types of sterilizers, while guaranteeing a good standard of sterilization, are infrequently employed because the substances they use tend to form residues on the instruments being sterilized. In particular, since said residues may cause infections or other similar problems in patients, they are removed by carefully and thoroughly rinsing the instruments which removes the residues but also increases the costs involved and results in less effective sterilization.

Another type of sterilizer are those which use radiation (UV radiation, γ-rays or microwaves) to disinfect medical equipment.

These sterilizers are also infrequently employed, owing to the high costs of production and of using such devices.

For the reasons outlined above, the most widely used sterilizers are steam sterilizers, also known as autoclaves, which, unlike those described above, are particularly economical to manufacture and to use and, above all, are simple to use and can easily be installed in laboratories thanks to their compact size.

The steam sterilizers currently known in the prior art comprise a main tank containing water; a sterilization chamber into which the instruments to be sterilized are placed; a feeding system suitable to draw water from the main tank, convert it into steam and convey it into the sterilization chamber; drying means, suitable to dry the equipment using, for example, a jet of hot air; and an evacuation system suitable to expel the waste fluid, that is the liquid and the residual gas/steam from the sterilization process.

Some examples of such steam sterilizers are described in U.S. Pat. No. 5,348,711 A, GB 1235952 A and U.S. Pat. No. 6,379,613.

The steam sterilizers are supplied with drinking water, that is water from the mains, which is not particularly opportune owing to the presence of microbial flora that is, however, generally harmless in terms of type and concentration (and is, in any case, eliminated during the sterilization process, although it does increase the risk of residual bacterial load).

Under certain conditions, for example in case of deterioration of the water supply mains, said microbial flora may include harmful micro-organisms which could give rise to serious complications if they came into contact with the mucous membranes or internal organs. The presence of an excessive concentration of said micro-organisms could therefore undermine the effectiveness of the sterilization process and increase the level of risk in comparison to normal conditions.

Moreover, when contaminated water is used in a sterilizer, biofilms develop inside the tubes and tank and this results in a gradual increase in the concentration of potentially harmful and definitely undesirable micro-organisms.

Lastly, the main problem associated with the use of ordinary drinking water is the presence of limescale and other suspended solid residues which eventually result in the build-up of scale deposits.

Said substances contain organic components, such as cellular debris and inorganic minerals, which act as nutrients and provide a growth substrate, thus fostering microbial expansion.

Moreover the scale deposits place the components of the hydraulic system (valves, pumps, etc.) at risk making them subject to faults, blockages and premature wear.

In an attempt to overcome the aforesaid problems, external systems are frequently used, usually reverse osmosis systems, in which a membrane is used to retain the solute and, thus, obtain sterilized water that is substantially mineral-free and therefore with low conductivity.

The reverse osmosis sterilization systems have some important drawbacks such as, for example, their high cost.

Another important drawback of the reverse osmosis systems is that their purifying capacity deteriorates quickly.

Another problem, linked to said drawback, lies in the fact that, since the water is not perfectly disinfected, the bacterial load could increase while the water stagnates in the main tank before being used, reducing the standard of sterilization achieved by the steam sterilizer.

Instead of the reverse osmosis systems described above, steam sterilizers may be equipped with an internal filter which filters the water as it flows from the main tank to the steam generator, thus reducing its conductivity and bacterial load.

In order to guarantee a good level of demineralisation and sterilization, said internal filter is made of high-performance materials, which are very expensive.

It is also large in size.

An important problem associated with sterilizers provided with an internal filter consists in the fact that said filter must be able to purify the water within a short time.

Thus, to guarantee a good level of demineralisation and sterilization, said internal filter is made of high-performance materials, which are very expensive. It is also large in size.

Another problem consists of the fact that the standard of sterilization guaranteed by the internal filter tends to deteriorate quickly and it therefore requires frequent maintenance.

Another no less important problem with the internal filter lies in the fact that it filters the water relatively slowly and thus considerably increases the sterilization cycle time.

To overcome said problem and guarantee a good filtering speed, such filters are usually particularly large, and thus very expensive.

In this situation the technical purpose of the present invention is to devise a steam sterilizer able to substantially overcome the drawbacks mentioned above.

Within the sphere of said technical purpose one important aim of the invention is to provide a steam sterilizer that is capable of guaranteeing a good standard of sterilization and low conductivity of the water used for the sterilization process.

Another important aim is to provide a steam sterilizer capable of ensuring a high level of purification and disinfection of the water, even after a large number of cycles, and which does not therefore require frequent maintenance.

The technical purpose and specified aims are achieved with a steam sterilizer as claimed in the appended Claim 1.

Preferred embodiments are described in the dependent claims.

The characteristics and advantages of the invention are clearly evident from the following detailed description of a preferred embodiment thereof, with reference to FIG. 1 which illustrates the steam sterilizer according to the invention.

With reference to said drawing, reference numeral 1 globally denotes the steam sterilizer according to the invention.

It implements and substantially comprises a sterilization system for medical equipment and, in particular, for dental instruments and similar equipment, which performs said sterilization by using a sterilization fluid 1a, normally demineralised water, in the form of steam and characterized by high pressure and temperature values.

The steam sterilizer 1 comprises a sterilization chamber 20 inside which the medical instruments are placed and sterilized; a feeding system 30 suitable to feed the sterilization chamber 20 with the sterilization fluid 1a; an evacuation system 40 suitable to evacuate a discharge fluid 1b from the sterilization chamber 20; and a purification system 50 suitable to draw at least one of the fluids 1a and 1b out of at least one of the systems 30 and 40, clean it and introduce it into the feeding system 30.

The sterilization chamber 20 typically consists of a small-volume container for medical instruments and, preferably, suitable for dental instruments and similar equipment. It is of the type known in the prior art and normally consists of a structure that is practically cylindrical in shape and made of stainless steel.

The feeding system 30 comprises a main tank 31 suitable to collect the sterilization fluid 1a; at least a first pump 32 suitable to move the sterilization fluid 1a between said tank 31 and said sterilization chamber 20; and a steam generation unit 33, of a kind known in the prior art and schematically illustrated in FIG. 1, suitable to convert the fluid 1a from liquid form to steam.

The main tank 31 is provided with specific test sensors 31a suitable to measure the biochemical characteristics of the sterilization fluid 1a. Such test sensors 31a may comprise conductivity metering devices that measure the microsiemens value of the sterilization fluid 1a in order to determine the conductivity of the fluid 11a by measuring the flow of current between two electrodes immersed in said fluid; and/or bacterial load measuring devices which, by means of flow cytometry or turbidimetry, determine the bacterial load of the fluid 1a and the endotoxin content.

It may also advantageously be provided with measuring means 31b suitable to measure the volume and pressure of the sterilization fluid 1a contained in said tank 21 so as to determine a minimum level and a maximum level of volume and pressure of the fluid 1a and, thus, to signal the presence of too much or, alternatively, too little sterilization fluid 1a.

The evacuation system 40 comprises an unloading tank 41 suitable to collect the discharge fluid 1b coming out of the sterilization chamber 20 and which may be fitted with an outlet 41a to discharge the fluid 1b into the environment; one or more solenoid valves 42 suitable to move the discharge fluid 1b from the sterilization chamber 20 to the unloading tank 41; a series of drainage pipes 43 suitable to place the unloading tank 41 and the sterilization chamber 20 into connection for fluid passage.

It is also provided with a vacuum pump 44 suitable to depressurise the unloading tank 41 in order to evacuate the gas in the unloading tank 41 and a filter 45 suitable to purify the gas drawn out by the vacuum pump 44 before being discharged into the environment via a secondary drainage pipe 45a.

In particular, the vacuum pump 44 draws in a mixture of air and steam from the unloading tank 41 lowering the pressure inside the tank 41 so as to facilitate the elimination of the gas dissolved in the discharge fluid 1b from said fluid and, at the same time, the evaporation of the discharge fluid 1b due to the lowering of the boiling point.

The filter 45 may comprise filtering membranes, for example made of resin, suitable to reduce the bacteria content of the gas so that when said gas is evacuated it is practically perfectly sanitized and, thus, not apt to contaminate the environment.

The unloading tank 41, like the main tank 31, is provided with second measuring means 41a suitable to measure the volume and pressure of the discharge fluid 1b contained in said tank 41 so as to determine a minimum level and a maximum level of volume and pressure of fluid 1b and, thus, signal at least a too full condition.

In addition to said systems 30 and 40, the sterilizer 1 comprises a purification system 50 suitable to draw at least one of the two fluids 1a and 1b out of the relative system 30 and 40, purify it and release it into the main tank 31.

Said purification system 50 comprises cleaning means 51 suitable to purify at least the sterilization fluid 1a; a drawing circuit 52 suitable to bring the main tank 31 and the cleaning means 51 into connection for fluid passage; and an unloading circuit 53 suitable to bring the means 51 and the tank 31 into connection for fluid passage.

The cleaning means 51 are suitable to purify at least the sterilization fluid 1a so as to lower the bacterial load and conductivity thereof. They thus comprise a first filtering means 51a suitable to disinfect the fluid, that is to lower the bacterial load by eliminating the bacteria and microorganisms present in the fluid 1a and a second filtering means 51b suitable to reduce the conductivity by removing the metals dissolved in the sterilization fluid 1a.

The first filtering means 51a is suitable to lower at least the bacterial load of the treated fluid and, in particular, to lower both the bacterial load and the endotoxin content of the treated fluid. It thus comprises a filtering element made of a polymeric material such as, for example, cellulose acetate, polyamide, polysulfone and polyacrylonitrile, or, alternatively, of an inorganic material such as, for example, cordierite, borosilicate glass and alumina. In particular, the first filtering means 51a comprises a filtering element made of inorganic material and, more particularly, of the membrane type. Preferably, the first filtering means 51a is a porous ceramic filter.

The second filtering means 51b comprises a filtering element made of resin or other similar material suitable to lower the conductivity of the treated fluid. In particular, the second filtering means 51b comprises a filtering element made of resin and, more in particular, ion-exchange resin which, by releasing cations and/or anions in the fluid, lowers the dissolved mineral content and, thus, reduces the conductivity of the fluid.

The drawing circuit 52 consists of a series of pipes suitable to draw the sterilization fluid 1a out of the main tank 31 and, thus, convey it directly to the cleaning means 51.

Alternatively, as shown in FIG. 1, it consists of a series of pipes suitable to convey the sterilization fluid 1a to the unloading tank 41 so as to cool the discharge fluid 1b before it reaches the cleaning means 51.

In this case, the circuit may thus comprise a heat exchanger 52a suitable to permit the sterilization fluid 1a to cool the discharge fluid 1b and consisting, for example, of a coil heat exchanger arranged within the tank 41 so that the heat is exchanged between the fluids 1a and 1b by conduction.

In order to fully exploit the use of the cleaning means 51, the purification system 50 may also comprise a second drawing circuit 54 suitable to bring the unloading tank 41 and cleaning means 51 into connection for fluid passage; a valve 55 suitable to regulate the flow towards the cleaning means 51; a pump 56 suitable to move the fluids 1a and 1b within the circuits 52, 53 and 54; and cooling means 57 suitable to cool the fluids 1a and 1b before they reach the cleaning means 51.

In particular, the valve 55 consists of a three-way valve suitable to alternate the passage of the fluids 1a and 1b so that the cleaning means 51 alternately filter the fluids 1a and 1b.

Alternatively, the valve 55 is suitable to mix the fluids 1a and 1b so as to permit the simultaneous filtering thereof. In particular, in this case the valve 55 may be provided with a thermostat suitable to regulate the flow of the fluids so that the temperature of the fluid flowing out of said valve 55 is maintained at less than a fixed threshold.

The steam sterilizer 1 may comprise an additional purification system 60 suitable to place the unloading system 40 in connection with the feeding system 30 and to clean the discharge fluid 1b before it is mixed with the sterilization fluid 1a.

Said additional purification system 60 comprises additional filtering means 61 provided with cleaning means 61a and 61b substantially the same as the filtering means 51a and 51b and suitable to purify said discharge fluid 1b; a secondary drawing circuit 62 suitable to bring the unloading tank 41 and the additional filtering means 61 into connection for fluid passage; a secondary unloading circuit 63 suitable to bring the main tank 31 and additional filtering means 61 into connection for fluid passage; and an additional pump 65 suitable to move the discharge fluid 1b within the additional system 60.

The additional purification system 60 may also comprise an additional cooling means 64 suitable to cool the discharge fluid 1b before it reaches the additional means 61; an additional valve 66, preferably a three-way valve, which, since it is arranged between the additional filtering means 61 and the tank 31, allows the operator to introduce the filtered discharge fluid 1b into the tank 21 or, alternatively, to evacuate it via an outlet 67.

Lastly, the steam sterilizer 1 may be provided with a degassing apparatus 70 suitable to eliminate the gas dissolved in at least the sterilization fluid 1a.

Said sterilization apparatus, not illustrated in the drawing, comprises, for example, a vessel 71 arranged between the heat exchanger 52a and the valve 55 so as to receive the fluid 1a once this has absorbed heat from the heat exchanger 52a; and an additional vacuum pump 72 suitable to evacuate the gas contained in the vessel 71 so as to lower the pressure therein and, thus, facilitate the separation of the sterilization fluid 1a from the gas dissolved therein. In particular, the additional vacuum pump 72 is suitable to direct the gas extracted from the sterilization fluid 1a into the filter 45 or other similar filter to be purified before being evacuated into the environment.

The invention implements a new process for sterilizing medical instruments.

Said process comprises a sterilization step in which the sterilization fluid 1a is drawn from the main tank and used to sterilize the medical instruments in the sterilization chamber 20; an evacuation step in which the discharge fluid 1b is evacuated from the sterilization chamber 20 and collected in the unloading tank 41; and a purification step in which at least one of the fluids 1a and 1b is appropriately cleaned.

First, the sterilizer 1 is prepared by filling the main tank 31 with the sterilization fluid 1a and then the sterilization fluid 1a is analysed using the test sensors 31a to test whether the fluid 1a has the required biochemical characteristics. In particular, the test sensors 31a test whether the fluid 1a has adequate conductivity and bacterial load values and, more in particular, whether the conductivity and bacterial load values and the endotoxin content comply with previously set values.

If said values are not ideal, the purification step is activated, in which, using the purification system 50, the sterilization system eliminates the gas dissolved in the sterilization fluid 1a, drawn from the main tank 31, after which said fluid 1a flows through the cooling means 57 in order to reach the ideal temperature for cleaning and is thus purified by the cleaning means 51 and then re-introduced into the main tank 31.

Once the fluid 1a in said tank 31 has the required biochemical characteristics, that is to say when the bacterial load and conductivity of the water, which constitutes the fluid 1a in the tank 31, are practically zero, the purification step is complete and the sterilization and unloading steps can be activated. In particular, said purification step may be interrupted when the sterilization fluid 1a has a conductivity value of substantially less than 15 microsiemens, more in particular, a conductivity of substantially less than 10 microsiemens, preferably substantially less than 5 microsiemens and, yet more preferably, substantially equal to 0 microsiemens. In detail, the step is interrupted when the fluid 1a has a temperature that is substantially comprised between 40° C. and 70° C., and preferably between 50° C. and 60° C.

Alternatively, the operator may set the purification step to be performed continuously. In other words, the purification step may be performed all the time, continuously, regardless of the bacterial load and conductivity of the fluid 1a in the main tank 31. In detail, in this case, the sterilization fluid 1a is continuously cleaned by the sterilization system 50 so as to prevent the fluid 1a from stagnating in the tank 31 and, at the same time, to maintain the conductivity and bacterial load at the ideal levels, i.e. practically zero.

Lastly, if, when the sterilization and evacuation steps have been performed a number of times, there is an insufficient level of sterilization fluid 1a in the main tank 31, or there is too much discharge fluid 1b in the tank 41, the purification step is activated, in which the discharge fluid 1b is converted into sterilization fluid 1a by means of cleaning and is then introduced into the main tank 31.

In this step, the purification system 50 draws the discharge fluid 1b from the unloading tank 41, adjusts the temperature thereof by means of the cooling means 57 and/or by mixing it with the sterilization fluid 1a from the main tank 31, purifies it using the cleaning means 51 and, lastly, introduces it into the main tank 31.

Moreover, in order to speed up the topping up of the main tank 31, the additional purification system 60 may also be activated which, in the same way as the system 50, cools the discharge fluid 1b by means of the additional cooling means 64, purifies it using the additional cleaning means 61 and then introduces it into the main tank 31.

Lastly, if the test sensors 31a detect a reduction in the speed at which the bacterial load, endotoxin content and/or conductivity are lowered, the sterilizer 1 signals, for example by means of specific optical/acoustic indicators, the need to replace one or more of the related filtering means 51a and 51b or one or more of the cleaning means 61a and 61b. In particular, if the sensors 31a do not detect any change in the parameters being measured, the sterilizer 1 signals the need to change one or more of said means 51a, 51b, 61a and 61b.

Once the sterilization fluid 1a in the main tank 31 is at the required level, the test sensors 31a analyse the biochemical characteristics of the sterilization fluid 1a in the main tank 31 again and, thus, decide whether said fluid is suitable for sterilizing or whether, if the fluid does not have the required biochemical characteristics, a new purification step is required.

The invention achieves some important advantages.

A first important advantage lies in the fact that the steam sterilizer 1 uses particularly small and conveniently-priced filtering means which achieve a high standard of sterilization while, at the same time, being extremely economical to manufacture and operate.

Said advantage has been obtained thanks to the innovative purification system 50 which, by defining a closed circuit, means that the sterilization fluid 1a flows through the cleaning means 51a large number of times so that the cleaning means 51 are able to process the sterilization fluid 1a several times, unlike with the prior art systems in which the fluid is cleaned in a single passage.

The possibility of cleaning the sterilization fluid 1a several times prevents any loss of efficiency of the means 51 and means that the steam sterilizer 1 requires very few maintenance operations and is thus reliable and has a long service life.

Said advantages in terms of costs and quality are further guaranteed by the presence of the cooling means 57 and of any additional cooling means 64 which cool the fluids 1a and 1b so that the sterilization fluid 1a can always be maintained at the ideal temperature for sterilization, thus optimising the operation of the means 51 and 61.

In particular, thanks to the presence of the cooling means 57 and 64, the fluid at the means 51 and 61 is always at the ideal temperature for filtering by the resins of the second filtering means 51b.

Said aspect is further guaranteed by the valve 55 which, by appropriately mixing the discharge fluid 1b and the sterilization fluid 1a, permits the adjustment of the temperature of the fluid entering the means 51 and, thus, facilitates the cleaning of the fluid.

Another advantage lies in the fact that since the sterilization fluid 1a can be purified at all times by the cleaning means 51, it always has the ideal biochemical characteristics and is not therefore subject to the deterioration typical of the known steam sterilizers.

An important advantage, given by the practically constant absence of bacterial load and conductivity in the sterilization fluid 1a, consists of the possibility of avoiding the formation of biofilms in the feeding system 30 and, thus, contamination of the sterilization fluid 1a before the sterilization step.

In particular, thanks to the means 51 and 61, the sterilizer 1 is capable of running a sterilization cycle using a fluid 1a with substantially no bacterial load and with a conductivity that is practically equal to 0 microsiemens.

Said aspect is further guaranteed by the possibility of performing the purification step continuously.

A further advantage consists of the fact that the purification systems 50 and 60 permit the discharge fluid 1b to be cleaned and, thus, used again for a new sterilization step. In particular, said possibility permits the steam sterilizer 1 to perform a practically infinite number of sterilization cycles, with a given amount of fluid, thus increasing the autonomy of the sterilizer 1.

A further advantage consists of the possibility of discharging the discharge fluid 1b into the environment once it has been cleaned. In detail, said aspect is guaranteed by the presence of the additional valve 67, which is arranged downstream of the additional means 61 and thanks to which the fluid 1b, after being cleaned, can be evacuated into the main tank 31 or, alternatively, to the outside via an outlet 67. Moreover, said solution may even be achieved by inserting a three-way valve and a drainage outlet, similar to the valve 66 and the outlet 67, between the cleaning means 51 and the tank 31.

A further and no less important advantage is that, as the discharge fluid 1b is not released into the environment, the steam sterilizer 1 avoids contamination of the environment outside the sterilizer 1.

Modifications and variations may be made to the invention described herein without departing from the scope of the inventive concept. All the elements as described and claimed herein may be replaced with equivalent elements and the scope of the invention includes all other details, materials, shapes and dimensions.

The invention claimed is:

1. A steam sterilizer for medical instruments, comprising:
    a feeding system configured to feed a sterilization chamber and comprising at least one main tank configured to contain a sterilization fluid and;
    an evacuation system configured to evacuate a discharge fluid from said sterilization chamber, comprising a purification system configured to draw at least one of said sterilization fluid and discharge fluid out of at least one of said feeding system and evacuation system and to introduce said at least one fluid into said at least one main tank, and said purification system comprising cleaning means configured to filter said at least one fluid;
    said purification system further comprising a drawing circuit configured to bring said at least one main tank and said cleaning means into connection for fluid passage; and an unloading circuit configured to bring said cleaning means and said at least one main tank into connection for fluid passage and a secondary drawing circuit configured to bring said evacuation system and said cleaning means into connection for fluid passage.

2. The steam sterilizer as claimed in claim 1, said evacuation system further comprising an unloading tank configured to contain said discharge fluid, and wherein said secondary drawing circuit is configured to bring said unloading tank and said cleaning means into connection for fluid passage.

3. The steam sterilizer as claimed in claim 1, said purification system further comprising a valve configured to enable said cleaning means to alternately filter said fluids.

* * * * *